(12) United States Patent
Cheramy et al.

(10) Patent No.: US 12,158,415 B2
(45) Date of Patent: Dec. 3, 2024

(54) DETECTION OF WATER CONTAMINATION BASED ON SPECTROGRAPHIC ANALYSIS

(71) Applicant: 2S Water Incorporated, Edmonton (CA)

(72) Inventors: Joseph John Cheramy, Edmonton (CA); Anders Jaques Palmgren, Edmonton (CA); Avro Anthony Sargeaunt Nelson, Esquimalt (CA); Anthony Brent Nelson, Edmonton (CA)

(73) Assignee: 2S Water Incorporated, Edmonton (CA)

( * ) Notice: Subject to any disclaimer, the term of this patent is extended or adjusted under 35 U.S.C. 154(b) by 173 days.

(21) Appl. No.: 17/719,033

(22) Filed: Apr. 12, 2022

(65) Prior Publication Data

US 2023/0324285 A1  Oct. 12, 2023

(51) Int. Cl.
  *G01N 21/31* (2006.01)
  *G01N 21/94* (2006.01)
  *G01N 33/18* (2006.01)

(52) U.S. Cl.
  CPC ............. *G01N 21/31* (2013.01); *G01N 21/94* (2013.01); *G01N 33/1826* (2013.01); *G01N 33/184* (2024.05)

(58) Field of Classification Search
  CPC ......... G01N 21/31; G01N 21/69; G01N 21/94
  See application file for complete search history.

(56) References Cited

U.S. PATENT DOCUMENTS

| | | | | |
|---|---|---|---|---|
| 4,998,914 A | * | 3/1991 | Wiest | A61M 3/022 604/153 |
| 5,383,019 A | * | 1/1995 | Farrell | G01N 21/73 250/288 |
| 2003/0103205 A1 | * | 6/2003 | Gianchandani | G01N 21/67 356/311 |
| 2008/0212074 A1 | * | 9/2008 | Goulter | G01J 3/0202 356/73 |
| 2015/0339635 A1 | * | 11/2015 | Washiro | G06Q 10/20 705/305 |
| 2016/0069798 A1 | * | 3/2016 | Yokoyama | G01N 33/54373 422/69 |
| 2016/0088809 A1 | * | 3/2016 | Lowe | A01G 24/44 47/59 S |
| 2023/0014558 A1 | * | 1/2023 | Sabry | B81B 7/02 |

FOREIGN PATENT DOCUMENTS

CN 103712973 A * 4/2014

* cited by examiner

Primary Examiner — Hina F Ayub
(74) Attorney, Agent, or Firm — Michael D. Eisenberg (57) ABSTRACT

A system for real-time spectrographic analysis for automatically identifying contaminants in water comprising: a spectrometer configured to process electromagnetic radiation emitted by a plasma created between a solid electrode and a liquid electrode; and a control node operatively connected to the spectrometer, the control node comprising a processor and a memory on which are stored machine-readable instructions that when executed by the processor, cause the processor to acquire spectroscopic data from the spectrometer and to analyze the spectroscopic data to determine concentration levels of contaminants in the water sample.

19 Claims, 6 Drawing Sheets

DETECTION OF WATER CONTAMINATION BASED ON SPECTROGRAPHIC ANALYSIS

TECHNICAL FIELD

This application generally relates to detection of contaminants in water, and more particularly, to an automated method of detection of water contamination based on real-time spectrographic analysis.

BACKGROUND

Water is often contaminated with a variety of harmful elements. The water contaminants may include pesticides, toxic metals, drugs, and various pharmaceuticals. Detecting these contaminants can involve the use of sensors or biosensors, among other solutions. In many instances, these solutions are not cost-effective and inefficient.

Detection of contaminants such as dissolved metals is an important step towards cleaning drinking water and eliminating the adverse health risks associated with polluted water. One of the most common techniques used to detect and identify dissolved metals contaminants in aquatic environments is the evaluation of water based on chemical analysis.

Generally, many common methods used to gauge dissolved contaminants in localized water sources are expensive, complex and costly. Traditionally, the analysis of water contamination is a laboratory process. A limited number of single-element detectors are available that offer real-time processing and detection of contaminants.

As such, what is needed is a solution for automated detection of water contamination based on real-time spectrographic analysis.

SUMMARY

One example embodiment provides a system for real-time spectrographic analysis for automatically identifying contaminants in water comprising: a spectrometer configured to process electromagnetic radiation emitted by a plasma created between a solid electrode and a liquid electrode; and a control node operatively connected to the spectrometer, the control node comprising a processor and a memory on which are stored machine-readable instructions that when executed by the processor, cause the processor to acquire spectroscopic data from the spectrometer and to analyze the spectroscopic data to determine concentration levels of contaminants in the water sample.

Another example embodiment provides a method that includes one or more of acquiring, by a control node, spectroscopic data from the spectrometer configured to process electromagnetic radiation emitted by a plasma created between a solid electrode and a liquid electrode, and analyzing, by the control node, the spectroscopic data to determine concentration levels of contaminants in the water sample.

DETAILED DESCRIPTION

It will be readily understood that the instant components, as generally described and illustrated in the figures herein, may be arranged and designed in a wide variety of different configurations. Thus, the following detailed description of the embodiments of at least one of a method, apparatus, non-transitory computer readable medium and system, as represented in the attached figures, is not intended to limit the scope of the application as claimed but is merely representative of selected embodiments.

The instant features, structures, or characteristics as described throughout this specification may be combined or removed in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment. Thus, appearances of the phrases "example embodiments", "in some embodiments", "in other embodiments", or other similar language, throughout this specification do not necessarily all refer to the same group of embodiments, and the described features, structures, or characteristics may be combined or removed in any suitable manner in one or more embodiments. Further, in the diagrams, any connection between elements can permit one-way and/or two-way communication even if the depicted connection is a one-way or two-way arrow. Also, any device depicted in the drawings can be a different device. For example, if a mobile device is shown sending information, a wired device could also be used to send the information.

In addition, while the term "message" may have been used in the description of embodiments, the application may be applied to many types of networks and data. Furthermore, while certain types of connections, messages, and signaling may be depicted in exemplary embodiments, the application is not limited to a certain type of connection, message, and signaling.

Example embodiments provide methods, systems, components, non-transitory computer readable media, devices, and/or networks, which provide for detection of water contamination based on real-time spectrographic analysis. In one embodiment, Optical Emission Spectroscopic Analysis of contaminants, such as dissolved metals, in liquids may be used.

In one embodiment, a universal sensor built for detecting dissolved metals and elemental contamination in water sources is provided.

Figure 1:
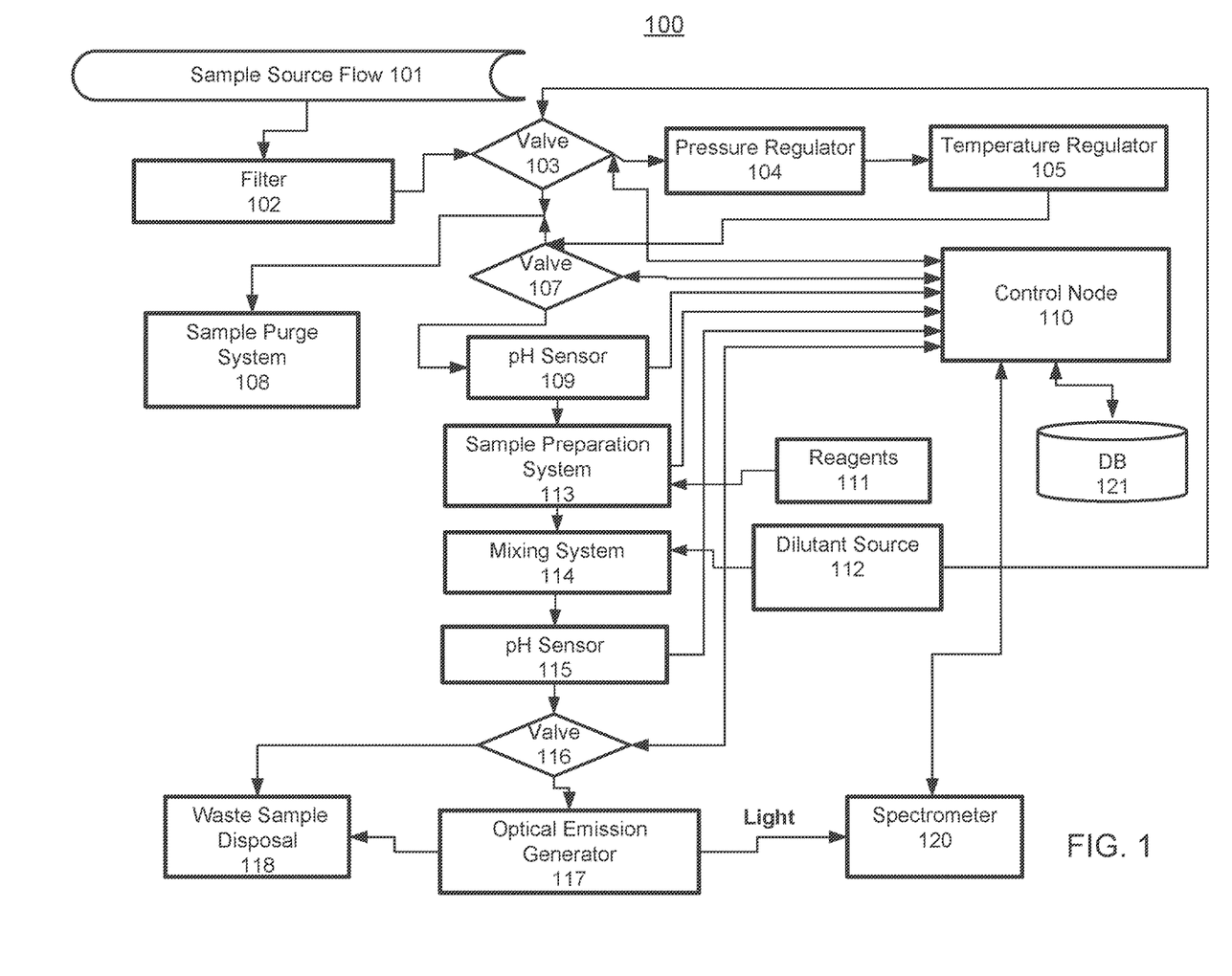
FIG. 1 illustrates a diagram of a system for automated detection of water contamination based on real-time spectrographic analysis, according to example embodiments.

FIG. 1 illustrates a system architecture 100 including a control node, according to the exemplary embodiments.

A flowing source line has a sample exit line 101. The sample exit line 101 may pass through a filter 102 to remove suspended solids, oils or other contaminants that interfere with the device. The filter 102 may be configured to allow occasional backflushing to clean the filter 102. Before the filter 102, or after the filter, the sample line 101 encounters a valve 103 that allows the sample line 101 from the source to the device to be flushed or purged through a sample purge system 108. In one position the valve 103 may direct the sample to the sensor, and in the other position the sample line 101 is allowed to flow to clear stale sample from the line between the source and the sensor.

The output of this line can go to waste, or can be recycled back into the source water. If the line is to go back into the source water, it is recommended that it returns to the source line after the sample exit line. At this point, it may be necessary to reduce the pressure from the line pressure to a pressure acceptable to the device, so a pressure reducing mechanism may be inserted. Also, at this point there may need to be a temperature correction to prevent the device from overheating. Temperature 105 and pressure correction 104 can result in precipitation from highly saturated solutions. If these units are in place, a source of diluent 112 should be available to reduce the concentration of contaminants in the sample. From time to time there would need to be a cleaning cycle where the pressure reducer and temperature reducer can be flushed, to clean out precipitated solids and flush them into the waste line. A valve 103 located before the temperature 105 and/or pressure 104 adjusting mechanism will switch between the source water and diluent 112 or a flushing solution. A valve 107 positioned after the temperature/pressure adjustment would switch between clearing to waste, or on to sample preparation system 113.

In the sample preparation area, there may be a pH sensor 109, and the mixing system 114 where the samples are measured and mixed with plasma conditioner which contains acids to adjust the pH of the sample and introduce other chemicals (i.e., reagents 111) as may be required to improve sensitivity. At this point, it may also be necessary to introduce additional diluent to reduce the concentration of the sample. This can be necessary when an element of interest has a high enough concentration to saturate the signal.

At this point, the sample, the plasma conditioner and the diluent in the correct proportions (variable based on the source of the sample) are mixed together in the mixing system 114. There may be a pH sensor 115 at this point to verify that the mixing system 114 has created a prepared sample at the correct pH. The mixed sample is fed into the plasma chamber at a specific rate. Any fluid not consumed in the plasma will drain out of the plasma chamber through the valve 116 and be pumped or gravity drained into the waste line 118. The optical emissions may be generated by the optical emission generator 117 by any method for causing the sample to emit electromagnetic emissions, or such other method known in the field for causing the sample components to emit light.

Air may be pumped through the plasma chamber. Air leaving the plasma chamber may be slightly acidic, and depending on the source water may contain hazardous chemicals. A filtering system may be present to remove hazardous vapors and to neutralize the acidity, or the air may be mixed with additional air and the result vented to atmosphere outside the building.

The waste line may be directed to the disposal 118, or alternately returned to the sample source. In one embodiment, the optical emission chamber causes the constituent elements in the sample to emit light using a method known in the field, the light from the chamber can be collected by a lens and directed to a fiber optic cable, or alternately directed directly into a spectrometer 120. The lens may be fixed or movable to allow the focal point to be directed to a particular part of the optical emission. The lens positioning can be manual or automated. The spectrometer 120 gathers the light and disperses the light into component wavelengths. The spectroscopic information can be analyzed on the device by a control node 110 or sent to a remote computer for analysis. The control node 110 may collect the spectroscopic data and may process the data along with the data received from other subsystems as shown in FIG. 1.

Within the Optical Emission Generator 117 emission is relatively diffuse, but is stronger in different regions of the plasma. An optical alignment system (not shown) can be incorporated to take advantage of these locations of concentration. Depending on the sensitivity desired for that element it may be advantageous to align the optics on the location within the plasma where the element concentrates. If it is desired to optimize for different elements an optical alignment system under the control of the control node 110 can move the alignment to optimize for a different element, and then re-align to the original location for other elements.

According to the exemplary embodiments, the device can prepare samples continuously or in small batches and processed frequently. The resulting analysis performed by the control node 110 may provide frequent readings suitable for use by a process control system. The analyzed results can be recorded onto a storage (e.g., DB 121) to provide a timeline analysis to identify trends in the contaminants.

The exemplary system is sensitive to changes in pH. A practitioner may choose the pH he wishes to operate the device at. However, it is critical that the pH is as consistent as possible for accurate measurement of the contaminants in the water. Due to this sensitivity, it is important to understand pH variability in the source water samples. If the pH values are consistently the same, then it is possible to operate without measuring the pH. However, if the pH varies, it may be necessary to measure the pH of the sample prior to calculating the ratios of the acidification agent and the sample. In one embodiment, this can be handled with a pH sensor at the start of the process, or a pH sensor at the end of the sample preparation process, or both. Often the client has value in knowing the pH of the source.

The samples are pumped through the exemplary sensor system and are mixed with the correct ratio of acidification agent (i.e., a plasma conditioner) to bring the pH to the correct value. An electric current is run from an electrode to a pool of the water that serves as a second electrode. An electrical connection is made, and the electrical power is chosen for breaking down the water and atmosphere to create a plasma. Any contaminants in the plasma will emit a characteristic set of frequencies. Each frequency (i.e., wavelength present in the emission line) will glow with a brightness that may be proportional to the quantity of the contaminant in the sample.

Initiation of the plasma requires either increasing the voltage or reducing the gap between the water and the electrode, or a combination of the two. The exemplary embodiments employ this method without a weir on the liquid electrode. When measuring the content of a contaminant it is possible for the elemental or ionic emission of the contaminant to be too bright to measure, overloading (i.e., saturating) the detector of the spectrometer. In that case, the pumping system adds diluent to dilute the sample in order to reduce the intensity to a measurable amount. The control node 110 may then compensate for the dilution to calculate the quantity of the contaminant. Occasionally, there will be another contaminant that will interfere with measuring the quantity of the contaminant. This would be another reason to dilute the sample before reading the quantity of the contaminant.

When measuring multiple contaminants, it may be advisable to run the sample at multiple dilution levels to optimize the sensitivity for individual contaminants. For example, while measuring sodium it may be necessary to dilute the sample to reach a concentration of the sodium which emits strongly, but that dilution could result in reducing the signal for nickel below the sensitivity of the device for nickel. To be able to quantify both contaminants the sensor device can run once with dilution to measure the sodium and again with no dilution or less dilution to measure the nickel.

Figure 2:
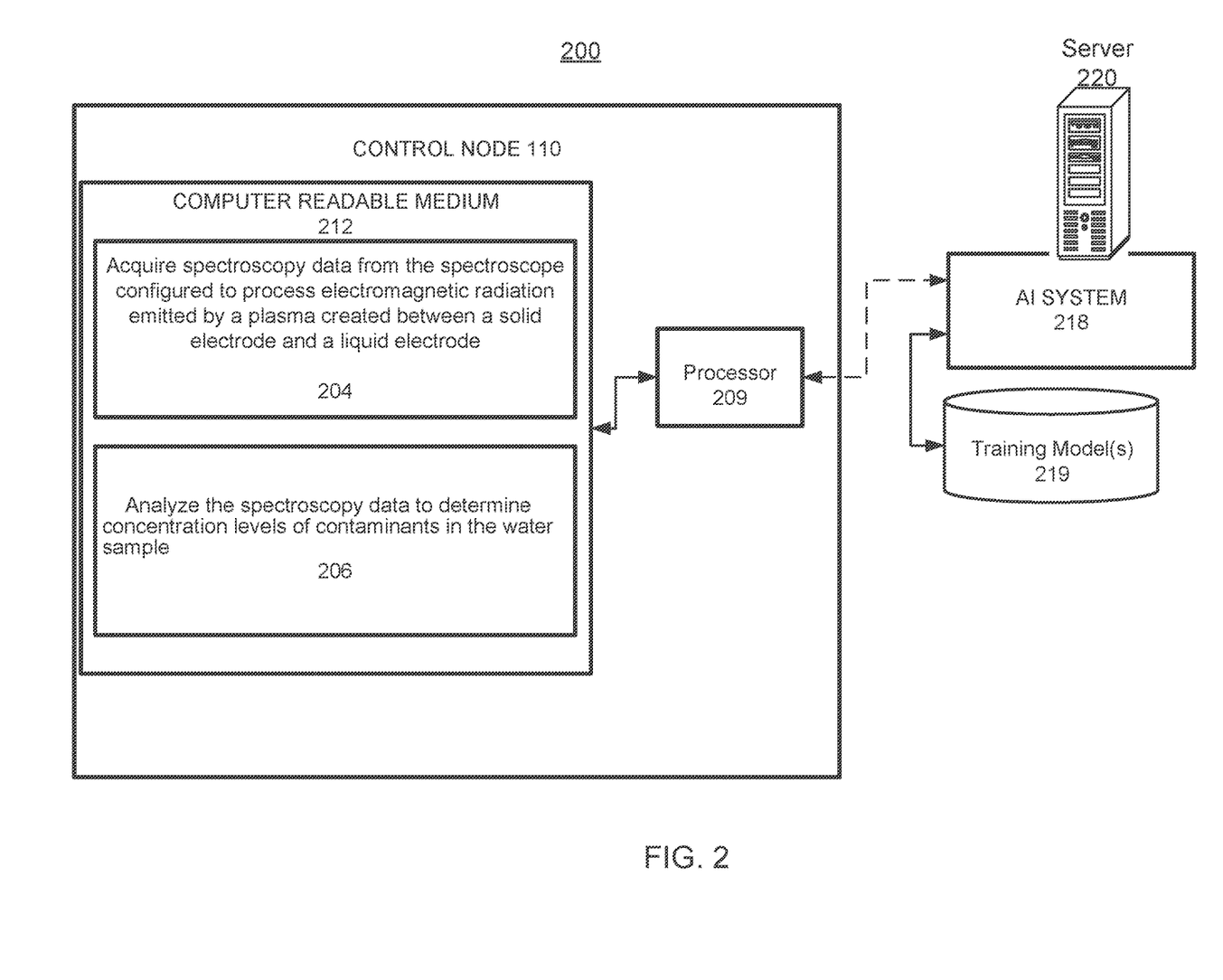
FIG. 2 illustrates a network diagram of a system including a detailed description of a control node and an AI system, according to example embodiments.

Conventional systems typically use an input from an operator who manually selects a line for an element and uses it to measure the quantity of that element. The exemplary embodiments employ the functionality of the control node 110 connected to the server 220 to measure multiple known lines for contaminants of interest and automatically select from the visible lines the ones that are most consistent. Whenever multiple good lines are visible at the spectrometer, all of them are measured. Lines with interferences with another contaminant are discarded.

According to the exemplary embodiments, the control node 110 may perform the following steps. A sample reading is taken on a timed cycle which is client specific whenever the device is active.

The steps are:
1. Turn on the spectrometer and take a dark reading of the spectrum. This represents the electrical noise generated by heat in the spectrometer, and incident radiation and cosmic rays.
2. Identify the pH and calculate the correct amount of an acidification agent to be added to result in the desired pH.
3. Set the pumping speed for the sample.
4. Set the pumping speed for acidification agent.

Note that the pumping speeds can be set to calculated values or may be determined by a Machine Learning Algorithm or other algorithms based on the historic information for this device.

5. Identify if dilution is required to measure all of the elements of interest.
6. Adjust the pumping speed for the sample.
7. Set the pumping speed for the water dilutant.

Note that dilution levels can be set to calculated values or be determined by a Machine Learning Algorithm or other algorithm(s) based on the historic information for the sensor device.

8. Run sufficiently prepared sample to fill the lines to the plasma chamber.
9. Turn on the high voltage, set the current and the initial voltage.
10. Ignite the plasma.
11. Observe the voltage and the current to determine when plasma stability has been achieved.
12. Turn on the spectrometer and take a measurement of the spectrum of the plasma.
13. Observe the voltage and current for the duration of the spectral reading. Any variations in the voltage or current indicate a failed reading.
14. Transmit the measured spectrum and the Dark spectrum reading to the server along with information about the state of the reading (good or failed). Failed readings are retained for diagnostic purposes.
15. Observe the spectrum to determine if a peak of interest has exceeded the maximum.
16. If the observed peak has reached the maximum, increase the dilution factor and take another Sample Reading with a higher dilution.
17. Turn off the high voltage, turn off the spectrometer and set Dilution back to default.
18. Wait for the timer to trigger the next cycle, then go to step 1.

According to the exemplary embodiments, a cleaning cycle is implemented as follows. A cleaning cycle is initiated at power up and before taking a sample reading or a calibration reading. Cleaning involves flushing the system with diluent to remove any remaining sample that may be in the lines. For particularly dirty water there may need to be multiple cleaning cycles initiated between samples in order to prevent cross contamination. The steps of the exemplary cleaning cycle are:

1. Change the source for the sample pump to the diluent source;
2. Pump through sufficient amount of diluent to clear the lines through to the plasma chamber;
3. Depending on the contaminants, at this point it may be necessary to flush continuously for a longer time period, and
4. Return the pump source to the sample line.

Note that while the sample pump is positioned to the diluent, the source line can be positioned to run to waste system to clear the source line of the stale sample. The sensor uses very small amounts of the sample. Even source water supply line of a small diameter can contain many times the amount used to take a reading. As such, it is necessary to allow the supply line to flow through to bring a current sample to the sensor for testing.

According to the exemplary embodiments, an Initiation Cycle is implemented as follows. When the device is powered up, it is in an unknown state. The control node is configured to force a known state and to make connection to the server before readings are taken.

1. The control node loads the operating system;
2. The control node determines that the device is in a safe state by:
   a. Verifying that the high voltage power is off;
   b. Verifying that the case is closed (if it has been opened, log the information into the device state storage);
   c. Setting of all pumps to dump to waste system;
   d. Resetting all of the pumps to initial state by clearing any fluid that may be in the pump;
   e. Establishing communications with the server;
   f. Downloading the configuration data for the device;
   g. Setting the source for each pump;
   h. Downloading the peaks of interest identified by the server;
   i. Reporting the device state to the server software and waiting for the instructions; and
   j. When the server sets the control node to active:
      i. Running a cleaning cycle; and
      ii. Running a sample reading.

According to the exemplary embodiments, a shutdown cycle is implemented as follows. The system shut down is initiated by the server. The shutdown cycle performs the steps of:

1. Set high voltage power off;
2. Turn off the spectrometer;
3. Set pumping input to air, and output to waste;
4. Clear the pumps and lines of fluid;
5. Inform the server of the state of the device;
6. Close the connection with the server and power down.

According to the exemplary embodiments, a Calibration Cycle is implemented as follows. Note that a typical calibration is implemented by creating multiple known samples and running them through the device. Each sample will have a known concentration of the contaminant of interest.

The exemplary embodiments, advantageously, use a single calibration sample having a known concentration above the highest expected concentration. The system then performs automatic dilution to create a number of measurement points at known concentrations. The calibration consists of the following steps:

1. The control node receives notification from the server that a calibration sample is in the system;
2. Sample source is set to the calibration sample;
3. Notify the server side of being ready to receive standard data. The server is informed that the next sample scan will be part of the calibration set;
4. A sample run is requested with no dilution;
5. Dilution ratio is incremented;
6. The server is informed of the dilution ratio;
7. A sample run is requested with dilution;
8. The server informs the control node if an additional point is needed. If an additional point is needed go to step 5 and if no additional step is required complete the calibration cycle.

According to the exemplary embodiments, a Scan Cycle is executed as follows. The Scan Cycle collects data from the control node of the device and places it in the database. That may trigger an analysis cycle to determine the concentrations and update the information in the database. In one embodiment, the control node may store data locally and may perform data analyses. The Scan Cycle may include the steps of:

1. Wait to receive a sample reading;
2. Verify that the sample reading is in the correct format. If not, flag a communications error and request a resend. If fails three times, abandon the reading, log the error (including the bad records) and exit;
3. Insert the sample reading into the database;
4. Perform the conversion from raw data to quantified concentrations for each of the elements the client has requested. Calculation of the conversion may be implemented by way of mathematical conversion or by way of a Machine Learning Algorithm (Machine Learning can take into account factors that are not used in the conversions and, thus, can correct for interferences or other factors that may influence the results) or by way of other algorithm(s).
5. Insert the quantification of the sample scan into the database.

FIG. 2 illustrates a diagram of a system 200 including a detailed description of a control node and an AI system, according to example embodiments.

As discussed above with reference to FIG. 1, the control node 110 is configured to collect and analyze spectroscopic information. The control node 110 may sent analytical data to the server 220 for further analysis. The control node 110 may collect the spectroscopic data and may process the data along with the data received from other subsystems as shown in FIG. 1.

The control node 110 may include additional components and that some of the components described herein may be removed and/or modified without departing from a scope of the control node 110 disclosed herein. The control node 110 may be a computing device or a server computer, or the like, and may include a processor 209, which may be a semiconductor-based microprocessor, a central processing unit (CPU), an application specific integrated circuit (ASIC), a field-programmable gate array (FPGA), and/or another hardware device. Although a single processor 209 is depicted, it should be understood that the control node 110 may include multiple processors, multiple cores, or the like, without departing from the scope of the control node 110.

The control node 110 may also include a non-transitory computer readable medium 212 that may have stored thereon machine-readable instructions executable by the processor 209. Examples of the machine-readable instructions are shown as 204-206 and are further discussed below. Examples of the non-transitory computer readable medium 212 may include an electronic, magnetic, optical, or other physical storage device that contains or stores executable instructions. For example, the non-transitory computer readable medium 212 may be a Random-Access Memory (RAM), an Electrically Erasable Programmable Read-Only Memory (EEPROM), a hard disk, an optical disc, or other type of storage device.

The processor 209 may execute the machine-readable instructions 204 to acquire spectroscopic data from the spectrometer 120 (FIG. 1) configured to process light (i.e., electromagnetic radiation from the near ultraviolet to visible energy range) emitted by a plasma created between a solid electrode and a liquid electrode. The processor 209 may execute the machine-readable instructions 206 to analyze the spectroscopic data to determine concentration levels of contaminants in the water sample.

As discussed above, the example system 100 for automated detection of water contamination based on real-time spectrographic analysis depicted in FIG. 1 may use inputs (e.g., contamination-related data) provided by an AI system 218 residing on a server node 220. In one embodiment, the AI system (i.e., module) 218 may reside on the control node 110 and may be executed by the processor 209. As discussed above, the pumping speed and dilution level settings may be acquired from an artificial intelligence (AI) system 218 based on historical data of the previous samples that had been analyzed. In one embodiment, the contamination of the sample may be predicted/determined by an AI system 218 training model 219 that uses data retrieved, for example, from a neural network (not shown) or from another source.

An AI system 218 residing on the server node 220 may be a computing device or a server computer, or the like, and may include a processor, which may be a semiconductor-based microprocessor, a central processing unit (CPU), an application specific integrated circuit (ASIC), a field-programmable gate array (FPGA), and/or another hardware device. Although a single processor is intended to be used, it should be understood that the AI system residing on the server node 220 may include multiple processors, multiple cores, or the like, without departing from the scope of the server node 220.

The server node 220 may also include a non-transitory computer readable medium that may have stored thereon machine-readable instructions executable by the processor to generate a training model(s) 219. Examples of the non-transitory computer readable medium may include an electronic, magnetic, optical, or other physical storage device that contains or stores executable instructions. For example, the non-transitory computer readable medium may be a Random-Access Memory (RAM), an Electrically Erasable Programmable Read-Only Memory (EEPROM), a hard disk, an optical disc, or other type of storage device.

The control node 110 may provide data received from the subsystems depicted in FIG. 1 along with spectroscopic data for comprehensive detection of contaminants in the sample. Thus, the system 100 for automated detection of water contamination based on real-time spectrographic analysis, advantageously, operates based on predictive data using optimal inputs from the AI system 218. In one embodiment, the pumping speed and dilution level settings of the system may be received by the control node 110 from the AI system 218.

Figure 3:
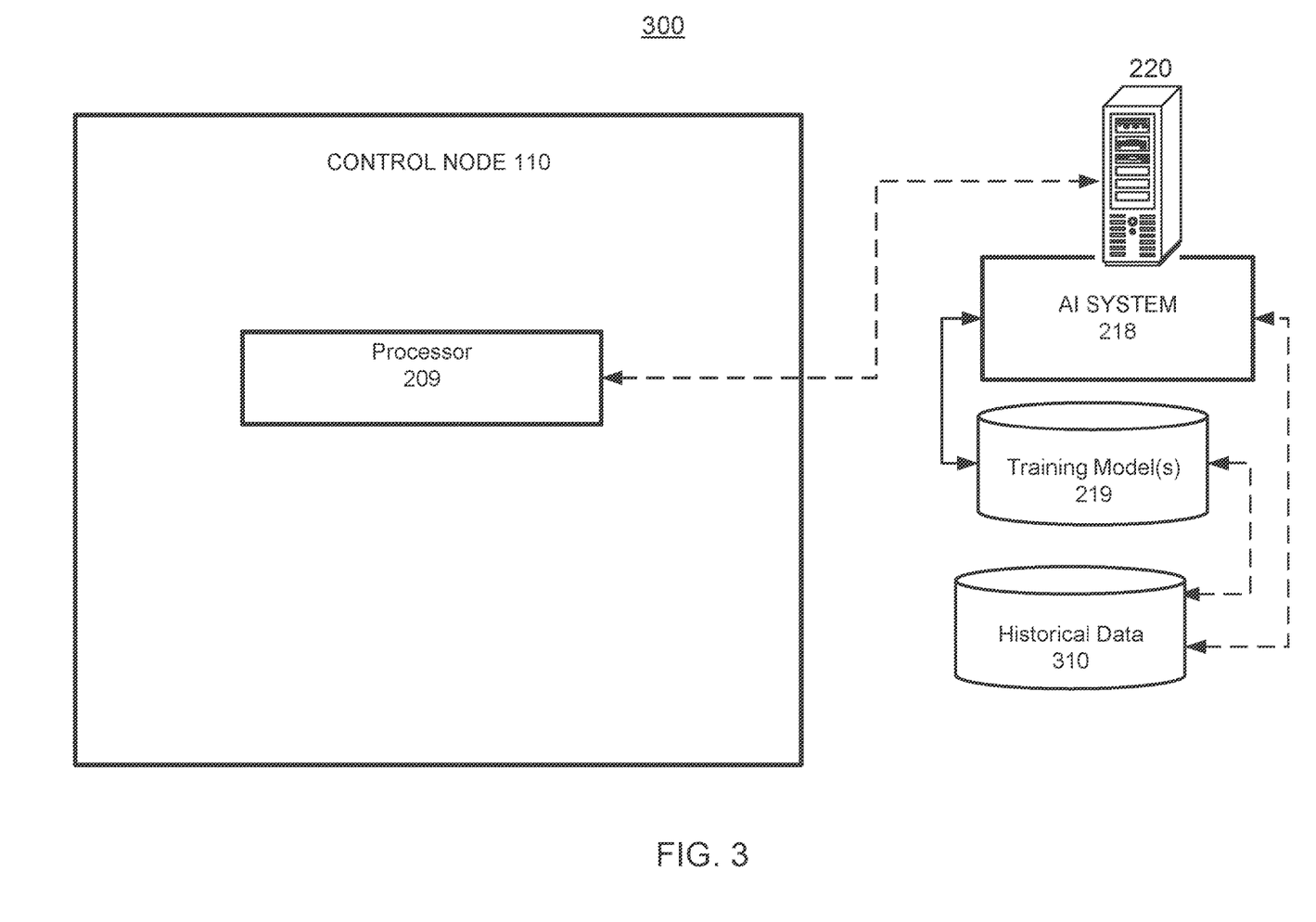
FIG. 3 illustrates a network diagram of a system including AI system and a database, according to example embodiments.

FIG. 3 illustrates a network diagram 300 of a system including AI system and a database of training samples, according to example embodiments.

As discussed above, the example system 100 for automated detection of water contamination based on real-time spectrographic analysis depicted in FIG. 1 may use inputs (e.g., contamination-related data) provided by an AI system 218 residing on a server node 220. In one embodiment, the AI system (i.e., module) 218 may reside on the control node 110 and may be executed by the processor 209. In another embodiment the values may be calculated programmatically from the calibration data.

As discussed above, the pumping speed and dilution settings may be acquired from an artificial intelligence (AI) system 218 based on historical data of other analyzed samples. The contamination of the sample may be predicted by the AI system 218 training model 219 that uses data retrieved, for example, from a neural network (not shown) or from another source 310. FIG. 3 illustrates a system 300 for automated detection of water contamination based on real-time spectrographic analysis that uses an input from an AI system based on data retrieved from a database 310, according to example embodiments.

As discussed above, the determination of water sample contamination may be executed by the AI system 218 based on the spectroscopic data received from the control node 110. In one embodiment, the contamination may be predicted/determined by the AI system 218 model 219 that uses data retrieved from the database 310. For example, optimal dilution levels and pumping speeds settings may be provided by the AI system 218 based on the historical data retrieved from a database 310.

Figure 4:
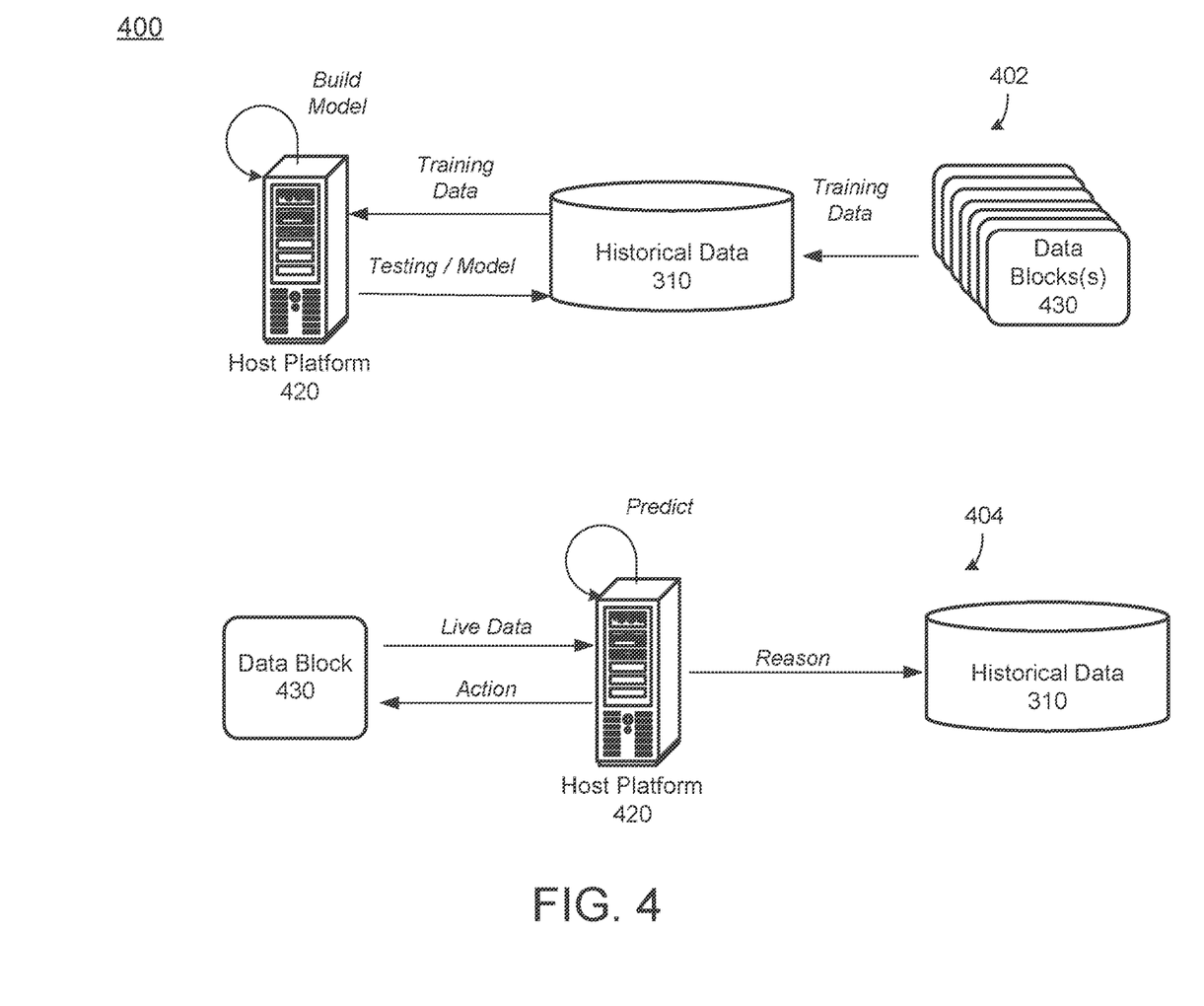
FIG. 4 illustrates how a database is used for learning model, according to example embodiments.

FIG. 4 illustrates an example 400 of a database 310 which stores machine learning (AI) data. Machine learning relies on vast quantities of historical data (or training data) to build predictive models for accurate prediction on new data. Machine learning algorithm may sift through millions of records to unearth non-intuitive patterns based on data retrieved from neural networks or from a database 310.

FIG. 4 illustrates how a database is used for learning model, according to example embodiments.

In the example depicted in FIG. 4, a host platform 420 builds and deploys a machine learning model for predictive monitoring of assets 430. Here, the host platform 420 may be a cloud platform, an industrial server, a web server, a personal computer, a user device, and the like. Assets 430 can represent, for example, pumping speed and dilution settings detection for contaminants.

The database 310 can be used to significantly improve both a training process 402 of the machine learning model and contamination predictive process 404 based on a trained machine learning model. For example, in 402, rather than requiring a data scientist/engineer or other user to collect the data, historical data may be stored by the data blocks 430 (or through an intermediary, not shown) on the database 310. This can significantly reduce the collection time needed by the host platform 420 when performing predictive model training. For example, data can be directly and reliably transferred straight from its place of origin (e.g., from the control node 110) to the database 310. By using the database 310 to ensure the security and ownership of the collected data, the data may be sent from the data block to the individuals that use the data for building a machine learning model. This allows for sharing of data among the data blocks 430.

The collected data may be stored in the database 310 based on a verification mechanism. The verification mechanism pulls in nodes to ensure that the data being recorded is verified and accurate. The data recorded may be time-stamped, cryptographically signed, and immutable. It is therefore auditable, transparent, and secure. In one embodiment, adding IoT devices (e.g., Hp sensors, thermometers, spectrometers, etc.) which write directly to the blocks on the database can increase both the frequency and accuracy of the data being recorded.

Furthermore, training of the machine learning model on the collected data may take rounds of refinement and testing by the host platform 420. Each round may be based on additional data or data that was not previously considered to help expand the knowledge of the machine learning model. In 402, the different training and testing steps (and the data associated therewith) may be stored on the database 310 by the host platform 420. Each refinement of the machine learning model (e.g., changes in variables, weights, etc.) may be stored on the database 310. This provides verifiable proof of how the model was trained and what data was used to train the model. Furthermore, when the host platform 420 has achieved a finally trained model, the resulting model data may be stored on the database 310 as well.

After the model has been trained, it may be deployed to a live environment where it can make optimal contamination-related predictions/determinations based on the execution of the final trained machine learning model. In this example, data fed back from the block 430 may be input into the machine learning model and may be used to make predictions such as optimal dilution and pumping speed or make a determination of contamination levels, etc. Determinations made by the execution of the machine learning model at the host platform 420 may be stored on the database 310 to provide auditable/verifiable proof. As one non-limiting example, the machine learning model may predict contamination based on optical emission as a part of the block 430. The data behind this decision may be stored by the host platform 420 on the database 310. The features and/or the actions described and/or depicted herein can occur on or with respect to the database 310.

Figure 5:
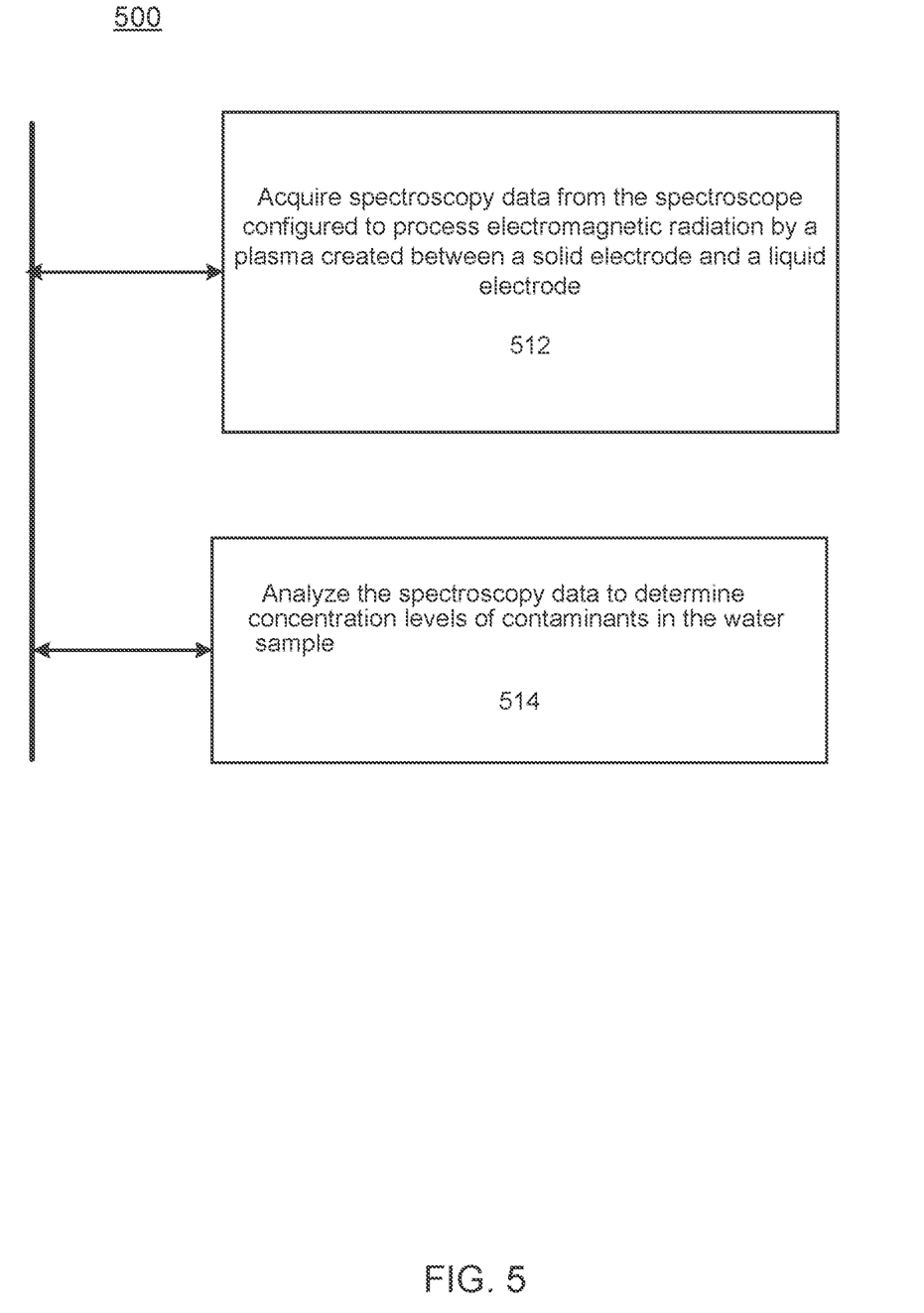
FIG. 5 illustrates a flow diagram, according to example embodiments.

FIG. 5 illustrates a flow diagram 500 of an example method, according to example embodiments. Referring to FIG. 5, the method 500 may include one or more of the steps described below.

FIG. 5 illustrates a flow chart of an example method executed by the control node 110 (see FIG. 1). It should be understood that method 500 depicted in FIG. 5 may include additional operations and that some of the operations described therein may be removed and/or modified without departing from the scope of the method 500. The description of the method 500 is also made with reference to the features depicted in FIG. 1 for purposes of illustration. Particularly, the processor 209 of the control node 110 may execute some or all of the operations included in the method 500.

With reference to FIG. 5, at block 512, the processor 209 may acquire spectroscopic data from the spectrometer configured to process electromagnetic radiation emitted between a solid electrode and a liquid electrode. At block 514, the processor 209 may analyze the spectroscopic data to determine concentration levels of contaminants in the water sample.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components.

Figure 6:
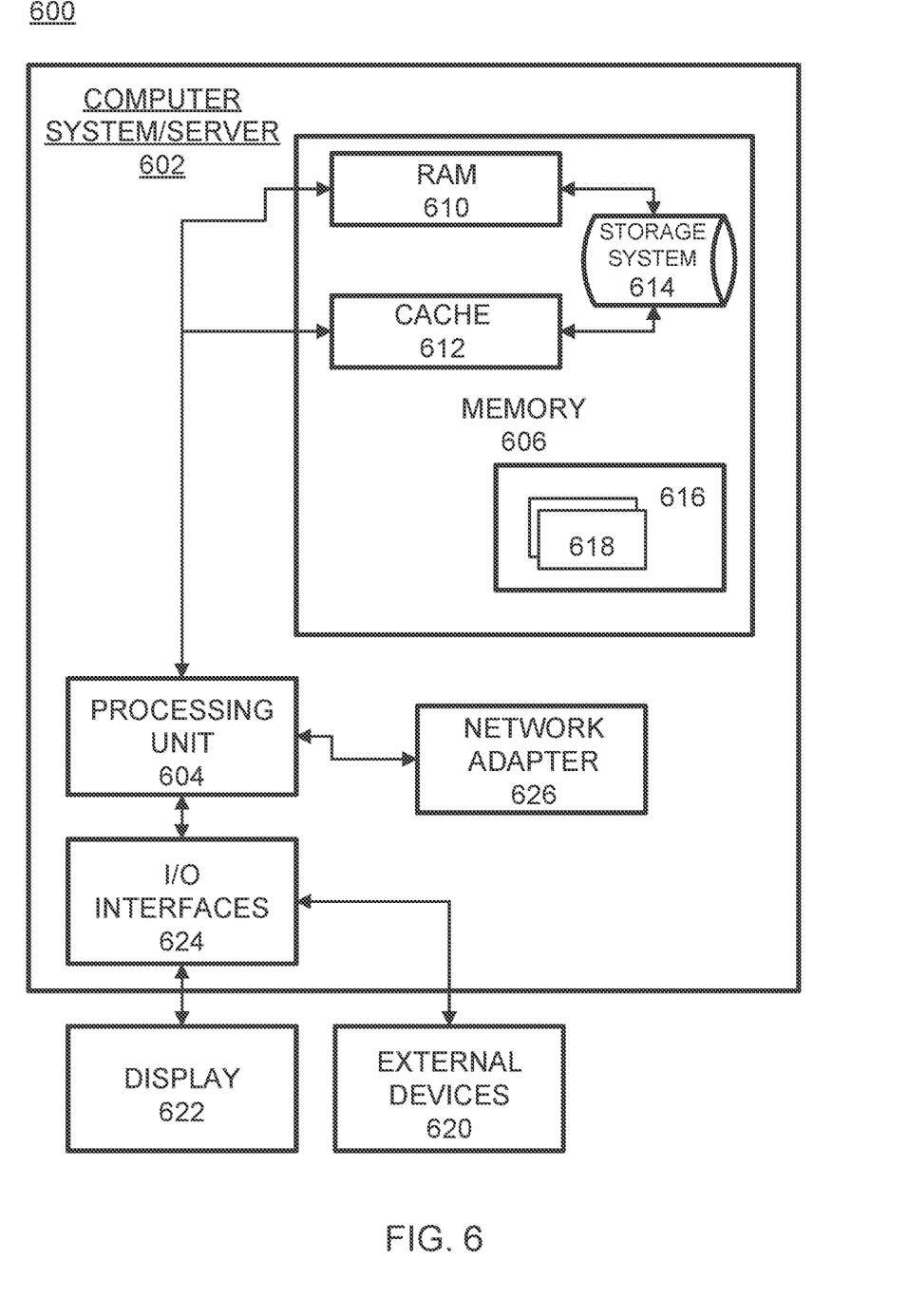
FIG. 6 illustrates an example node that supports one or more of the example embodiments.

FIG. 6 illustrates an example content processing node 600 that supports one or more of the example embodiments described and/or depicted herein. The content processing node 600 comprises a computer system/server 602, which is operational with numerous other general purposes or special purpose computing system environments or configurations. Examples of well-known computing systems, environments, and/or configurations that may be suitable for use with computer system/server 602 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system/server 602 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 602 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 602 in the content processing node 600 is shown in the form of a general-purpose computing device. The components of computer system/server 602 may include, but are not limited to, one or more processors or processing units 604, a system memory 606, and a bus that couples various system components including system memory 606 to processor 604.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 602 typically includes a variety of computer system readable media. Such media may be any available media that is accessible by computer system/server 602, and it includes both volatile and non-volatile media, removable and non-removable media. System memory 606, in one embodiment, implements the flow diagrams of the other figures. The system memory 606 can include computer system readable media in the form of volatile memory, such as random-access memory (RAM) 610 and/or cache memory 612. Computer system/server 602 may further include other removable/non-removable, volatile/non-volatile computer system storage media. By way of example only, storage system 614 can be provided for reading from and writing to a non-removable, non-volatile magnetic media (not shown and typically called a "hard drive"). Although not shown, a magnetic disk drive for reading from and writing to a removable, non-volatile magnetic disk, and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 606 may include at least one program product having a set (e.g., at least one) of program modules that are configured to carry out the functions of various embodiments of the application.

Program/utility 616, having a set (at least one) of program modules 618, may be stored in memory 606 by way of example, and not limitation, as well as an operating system, one or more application programs, other program modules, and program data. Each of the operating system, one or more application programs, other program modules, and program data or some combination thereof, may include an implementation of a networking environment. Program modules 618 generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

Computer system/server 602 may also communicate with one or more external devices 620 such as a keyboard, a pointing device, a display 622, etc.; one or more devices that enable a user to interact with computer system/server 602; and/or any devices (e.g., network card, modem, etc.) that enable computer system/server 602 to communicate with one or more other computing devices. Such communication can occur via I/O interfaces 624. Still yet, computer system/server 602 can communicate with one or more networks such as a local area network (LAN), a general wide area network (WAN), and/or a public network (e.g., the Internet) via network adapter 626. As depicted, network adapter 626 communicates with the other components of computer system/server 602 via a bus. It should be understood that although not shown, other hardware and/or software components could be used in conjunction with computer system/server 602. Examples, include, but are not limited to: microcode, device drivers, redundant processing units, external disk drive arrays, RAID systems, tape drives, and data archival storage systems, etc.

Although an exemplary embodiment of at least one of a system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A system for real-time spectrographic analysis for automatically identifying contaminants in water comprising:
   an optical emission spectrometer configured to process electromagnetic radiation emitted by a plasma created between a solid electrode and a liquid electrode; and
   a control node operatively connected to the optical emission spectrometer, the control node comprising a processor and a memory on which are stored machine-readable instructions that when executed by the processor, cause the processor to:
   acquire spectroscopic data from the optical emission spectrometer;
   analyze the spectroscopic data to determine concentration levels of contaminants in a water sample;
   determine acidity of the water sample by acquiring a reading of at least one pH sensor and to calculate a correct amount of an acidification agent to be added to the water sample to achieve a desired acidity level; and
   send a command to pump the water sample with the added acidification agent to fill a plurality of lines to a plasma chamber.

2. The system of claim 1, wherein the instructions further cause the processor to acquire a dark reading of a spectrum that represents an electrical noise generated by heat in the optical emission spectrometer and incident radiation and cosmic rays.

3. The system of claim 1, wherein the instructions further cause the processor to set pumping speeds for the water sample and for an acidification agent.

4. The system of claim 3, wherein the pumping speeds are acquired from an AI module configured to use historical data of the system.

5. The system of claim 1, wherein the instructions further cause the processor to send a command to turn on high voltage and to set an electric current and an initial voltage to ignite the plasma.

6. The system of claim 5, wherein the instructions further cause the processor to, responsive to determination of stability of the plasma based on monitoring of the voltage and the electric current, turn on the optical emission spectrometer and acquire a measurement of a spectrum of the plasma.

7. The system of claim 6, wherein the instructions further cause the processor to monitor the voltage and the electric current for a duration of reading of the spectrum, wherein any variations in the voltage or in the electric current indicate a failed reading.

8. The system of claim 6, wherein the instructions further cause the processor to, responsive to a determination that a peak of interest has exceeded a maximum, send a command to increase a dilution factor of the water sample and acquire a sample reading.

9. The system of claim 6, wherein the instructions further cause the processor to transmit the measurement of the spectrum of the plasma and the dark spectrum reading to a server connected to the control node along with information about a state of the readings, wherein failed readings are retained for diagnostic purposes.

10. The system of claim 1, wherein the instructions further cause the processor to provide the spectroscopic data to an AI system configured to generate a predictive model to determine the concentration levels of the contaminants in the water sample.

11. The system of claim 1, wherein the instructions further cause the processor to send commands to an optical alignment system to position light collection to an optimal position for a particular element to be measured.

12. A method, comprising:
    acquiring, by a control node, spectroscopic data from an optical emission spectrometer configured to process electromagnetic radiation emitted by a plasma created between a solid electrode and a liquid electrode; and
    analyzing, by the control node, the spectroscopic data to determine concentration levels of contaminants in a water sample; and
    monitoring voltage and an electric current for a duration of a reading of the spectroscopic data, wherein any variations in the voltage or in the electric current indicate a failed reading.

13. The method of claim 12, further comprising providing the spectroscopic data to an AI system configured to generate a predictive model to determine the concentration levels of the contaminants in the water sample.

14. The method of claim 12, further comprising acquiring a dark reading of a spectrum that represents an electrical noise generated by heat in the optical emission spectrometer and incident radiation and cosmic rays.

15. The method of claim 14, further comprising transmitting the measurement of the spectrum of the plasma and the dark spectrum reading to a server connected to the control node along with information about a state of the readings, wherein failed readings are retained for diagnostic purposes.

16. The method of claim 12, further comprising determining acidity of the water sample by acquiring a reading of at least one pH sensor and to calculate a correct amount of an acidification agent to be added to the water sample to achieve a desired acidity level.

17. The method of claim 16, further comprising, responsive to a determination that a peak of interest has exceeded a maximum, sending a command to increase a dilution factor of the water sample and acquire a sample reading.

18. The method of claim 17, further comprising, sending a command to pump the water sample with the increased dilution factor to fill a plurality of lines to a plasma chamber.

19. A system for real-time spectrographic analysis for automatically identifying contaminants in water comprising:
    an optical emission spectrometer configured to process electromagnetic radiation emitted by a plasma created between a solid electrode and a liquid electrode; and
    a control node operatively connected to the optical emission spectrometer, the control node comprising a processor and a memory on which are stored machine-readable instructions that when executed by the processor, cause the processor to:
    acquire spectroscopic data from the optical emission spectrometer;
    analyze the spectroscopic data to determine concentration levels of contaminants in a water sample;
    send a command to turn on high voltage and to set an electric current and an initial voltage to ignite the plasma;
    turn on the optical emission spectrometer and acquire a measurement of a spectrum of the plasma, responsive to determination of stability of the plasma based on monitoring of the voltage and the electric current; and
    monitor the voltage and the electric current for a duration of reading of the spectrum, wherein any variations in the voltage or in the electric current indicate a failed reading.

* * * * *